United States Patent [19]
Behler et al.

[11] Patent Number: 6,008,392
[45] Date of Patent: Dec. 28, 1999

[54] PROCESS FOR PREPARING ALKOXYLATED FATTY ACID ALKYL ESTERS

[75] Inventors: Ansgar Behler, Bottrop; Almud Folge, Langenfeld, both of Germany

[73] Assignee: Henkel Kommanditgesellschaft auf Aktien, Duesseldorf, Germany

[21] Appl. No.: 09/155,432

[22] PCT Filed: Mar. 18, 1997

[86] PCT No.: PCT/EP97/01339
§ 371 Date: Sep. 28, 1998
§ 102(e) Date: Sep. 28, 1998

[87] PCT Pub. No.: WO97/35831
PCT Pub. Date: Oct. 2, 1997

[30] Foreign Application Priority Data

Mar. 27, 1996 [DE] Germany .................. 196 11 999

[51] Int. Cl.$^6$ .................................. C07C 51/00
[52] U.S. Cl. ............................... 554/149; 554/148
[58] Field of Search ........................ 554/148, 149

[56] References Cited

U.S. PATENT DOCUMENTS 5,292,910  3/1994  Raths et al. .................. 554/149

FOREIGN PATENT DOCUMENTS

| 89 33349 | 10/1989 | Australia . |
| 0 339 426 | 11/1989 | European Pat. Off. . |
| 0523 089 | 1/1993 | European Pat. Off. . |
| 0 339 425 | 3/1994 | European Pat. Off. . |
| 44 46064 | 6/1995 | Germany . |

OTHER PUBLICATIONS

Weil, et al., J. Am. Oil. Chem. Soc., Sep., 1979, vol. 56, pp. 873–877.

Hama, et al., J. Am. Oil. Chem. Soc. AOCS Press (1995), vol. 72, No. 7, pp. 781–784.

*Primary Examiner*—Deborah D Carr
*Attorney, Agent, or Firm*—Ernest G. Szoke; Wayne C. Jaeschke; Steven J. Trzaska

[57] ABSTRACT

A process for making alkoxylated fatty acid alkyl esters involving: (a) providing a fatty acid alkyl ester; (b) providing an alkylene oxide component; (c) providing a primary catalyst; (d) providing a co-catalyst selected from the group consisting of lithium hydroxide, an alkaline earth metal, a tin salt and mixtures thereof; and (e) reacting (a)–(d) to make the alkoxylated fatty acid alkyl ester.

8 Claims, No Drawings

PROCESS FOR PREPARING ALKOXYLATED FATTY ACID ALKYL ESTERS

The application is a 371 of PCT/EP 97/01339 filed Mar. 18, 1997

BACKGROUND OF THE INVENTION

This invention relates to a process for the alkoxylation of fatty acid alkyl esters in the presence of double-layer mixed oxides and selected co-catalysts.

DISCUSSION OF RELATED ART

Alkoxylated alkyl esters, preferably so-called methyl ester ethoxylates, are known nonionic surfactants which have recently acquired considerable interest by virtue of their excellent washing performance. Relevant reviews can be found, for example, in J. Am. Oil Chem. Soc. 56, 873 (1979) and in J. Am. Oil Chem. Soc. 72, 781 (1995).

The addition of alkylene oxides onto compounds containing acidic hydrogen atoms, preferably onto primary alcohols, can be carried out in the presence of various, generally alkaline catalysts. Typical examples are potassium hydroxide or sodium methylate, which are added in the form of alcoholic solutions, or heterogeneous layer compounds of the hydrotalcite type which are introduced into the reaction mixture in the form of solids. By contrast, the insertion of alkylene oxides into the carbonyl ester bond is far more difficult and can only be achieved using special catalysts.

The use of calcined or fatty-acid-modified hydrotalcites for the alkoxylation of fatty acid esters is known from EP-B1 0 339 425 and EP-B1 0 523 089 (Henkel). According to DE-A1 44 46 064 (Lion), the ethoxylation of methyl esters is carried out in the presence of mixed metal oxides which have been surface-modified with metal hydroxides or metal alkoxides. However, these processes are unsatisfactory for operation on an industrial scale because, where methyl esters are used, a significant proportion of the starting material always remains unreacted and small amounts of methyl monoglycol esters, from which methyl glycol can be released by hydrolysis, are formed. In many cases, the homolog distribution is also unsatisfactory because it does not have a pronounced maximum and comprises excessive proportions of species with relatively low and relatively high degrees of ethoxylation.

Accordingly, the problem addressed by the present invention was to provide new catalysts for the production of alkoxylated alkyl esters with a narrow homolog distribution which would be free from unreacted alkyl esters and alkyl monoglycol esters.

DESCRIPTION OF THE INVENTION

The present invention relates to a process for the production of alkoxylated fatty acid alkyl esters corresponding to formula (I):

(I)

where $R^1CO$ is a linear or branched acyl group containing 6 to 22 carbon atoms and 0 and/or 1, 2 or 3 double bonds, $R^2$ is hydrogen or a methyl group, $R^3$ is a linear or branched alkyl group containing 1 to 22 carbon atoms and n is a number of—on average—1 to 20, in which fatty acid esters are reacted with ethylene and/or alkylene oxides in the presence of double-layer mixed-oxide catalysts, characterized in that co-catalysts selected from the group consisting of lithium hydroxide, alkaline earth metal salts and tin salts are used.

It has surprisingly been found that, by adding the co-catalysts mentioned to the known double-layer mixed-oxide catalysts, more particularly of the hydrotalcite type, the proportion both of unreacted alkyl esters and of alkyl monoglycol esters is significantly reduced. At the same time, a particularly narrow homolog distribution is obtained.

Fatty Acid Alkyl Esters

The fatty acid alkyl esters used as starting materials correspond to formula (II):

$$R^1CO-OR^3 \qquad (II)$$

where $R^1CO$ and $R^3$ are as defined above. The esters are derived from saturated and/or unsaturated fatty acids containing 6 to 22 and preferably 12 to 18 carbon atoms and alcohols containing 1 to 22 and preferably 1 to 4 carbon atoms. Typical examples are methyl, ethyl, propyl, butyl and/or stearyl esters of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils or in the reduction of aldehydes from Roelen's oxosynthesis. Cocofatty acid and/or tallow fatty acid methyl esters are preferably used as starting materials.

Catalysts

Suitable catalysts are, for example, the calcined or fatty-acid-modified hydrotalcites mentioned at the beginning which are described in detail in European patents EP-B1 0 339 425 and EP-B1 0 523 089. The teachings of these two documents are hereby specifically included in the teaching of the present application. The catalysts are used in quantities of normally 0.1 to 10% by weight and preferably 0.5 to 3% by weight, based on the alkoxylation products.

Co-catalysts

Besides the particularly preferred lithium hydroxide, suitable co-catalysts are calcium salts such as, for example, calcium carbonate, magnesium salts such as, for example, magnesium oxide, magnesium carbonate or magnesium acetate, barium salts such as, for example, barium-2-ethyl hexanoate and/or tin salts such as, for example, tin(IV) oxide. The co-catalysts are used in quantities of normally 0.01 to 0.5% by weight and preferably 0.1 to 0.2% by weight, based on the alkoxylation products.

Alkoxylation

The alkoxylation reaction may be carried out in known manner. To this end, the alkyl ester is normally introduced into a stirrer-equipped autoclave and the catalyst is subsequently added. It has proved to be of advantage to purge the autoclave thoroughly with nitrogen before the reaction to remove all traces of atmospheric oxygen. The autoclave is then heated. The alkoxylation reaction is carried out at temperatures of preferably 140 to 180° C. and more preferably 160 to 170° C. The alkylene oxide, which may be ethylene oxide, propylene oxide or mixtures of both, is introduced into the reactor by a siphon. The autogenous pressure can rise to about 5 bar. The alkylene oxide, preferably ethylene oxide, is preferably used in a quantity of on average 1 to 20 moles and more preferably 8 to 15 moles per mole of alkyl ester. The addition of the alkylene oxide is statistical, i.e. the insertion is not a highly selective reaction in which 1 mole of fatty acid alkyl ester reacts with exactly n moles of alkylene oxide. Instead, a complex mixture of esters alkoxylated to different degrees is obtained. The reaction is over when the pressure in the reactor falls to about 0.5 bar. For safety reasons, it is advisable to stir the mixture for another 30 minutes before the reactor is cooled and vented.

Commercial Applications

The alkoxylated fatty acid alkyl esters obtainable by the process according to the invention are substantially free from unreacted alkyl esters and alkyl monoglycol esters. In addition, they are distinguished by a particularly advantageous narrow homolog distribution. They are suitable, for example, for the production of laundry detergents, dishwashing detergents and cleaners.

EXAMPLES

General procedure. 256 g (1 mole) of technical lauric acid methyl ester were introduced into a 1-liter stirred autoclave and the proposed quantity of catalyst was added. The autoclave was closed and then alternately purged with nitrogen and evacuated three times to rule out the presence of atmospheric oxygen. The reaction mixture was then heated to 165° C. under a nitrogen blanket and 528 g (12 moles) of ethylene oxide were introduced in portions, the autogenous pressure initially rising to 3.5 bar. The reaction was continued until the pressure had fallen to 0.5 bar. After stirring for another 30 minutes, the autoclave was cooled and vented. The content of unreacted methyl ester (ME), the sum of unwanted lower homologs with 1 to 5 moles of ethylene oxide units (ME1/5) and the content of monomethyl glycol ester (MGE) are shown as quality criteria in Table 1. The quantities of catalysts and co-catalysts used are based on the end product.

TABLE 1

Ethoxylation of lauric acid methyl ester

| Ex. | Catalyst | [Cat.] % by wt. | Co-catalyst | [Co-cat.] % by wt. | ME % | ME 1/5 % | MGE ppm |
|---|---|---|---|---|---|---|---|
| C1 | Hydrotalcite, calc. | 0.50 | None | — | 2.2 | 15.5 | 20 |
| C1 | Hydrotalcite, calc. | 1.25 | None | — | 1.7 | 12.0 | 20 |
| 1 | Hydrotalcite, calc. | 1.12 | Lithium hydroxide | 0.13 | <0.1 | <0.1 | <1 |
| 2 | Hydrotalcite, calc. | 1.12 | Magnesium carbonate | 0.13 | <0.1 | 1.5 | <1 |
| 3 | Hydrotalcite, calc. | 1.12 | Magnesium acetate | 0.13 | <0.1 | 1.5 | <1 |
| 4 | Hydrotalcite, calc. | 1.12 | Tin(IV) oxide | 0.13 | <0.1 | 1.3 | <1 |

It can be seen that the addition of the co-catalysts according to the invention not only reduces the free methyl ester content to zero, it also significantly reduces the low-ethoxylated homologs, resulting in a narrow homolog distribution. At the same time, the quantity of methyl monoglycol ester is reduced below the detection limit.

We claim:

1. A process for making alkoxylated fatty acid alkyl esters corresponding to formula

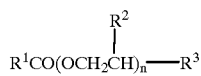

wherein $R^1CO$ is a linear or branched acyl group containing from 6 to 22 carbon atoms and up to 3 double bonds, $R^2$ is hydrogen or a methyl group, $R^3$ is a linear or branched alkyl group containing from 1 to 22 carbon atoms and n is a number of from 1 to 20, the process comprising:

(a) providing a fatty acid alkyl ester;
(b) providing an alkylene oxide component;
(c) providing a primary catalyst;
(d) providing a co-catalyst selected from the group consisting of lithium hydroxide, an alkaline earth metal, a tin salt and mixtures thereof; and
(e) reacting (a)–(d) to make the alkoxylated fatty acid alkyl ester.

2. The process of claim 1 wherein the primary catalyst is selected from the group consisting of a calcined hydrotalcite, a hydrotalcite hydrophobicized with a fatty acid and mixtures thereof.

3. The process of claim 1 wherein the primary catalyst is employed in a quantity of from 0.1 to 10% by weight, based on the weight of the alkoxylated fatty acid alkyl ester.

4. The process of claim 1 wherein the co-catalyst is selected from the group consisting of magnesium carbonate, magnesium acetate, tin oxide and mixtures thereof.

5. The process of claim 1 wherein the co-catalyst is employed in a quantity of from 0.01 to 0.5% by weight, based on the weight of the alkoxylated fatty acid alkyl ester.

6. The process of claim 1 wherein the reaction is carried out at a temperature of from 140 to 180° C.

7. The process of claim 1 wherein the alkylene oxide component is ethylene oxide.

8. The process of claim 1 wherein the alkylene oxide component is employed in a quantity of from 1–20 moles of alkylene oxide per mole of alkyl ester.

* * * * *